(12) United States Patent
Jafri

(10) Patent No.: US 11,324,657 B2
(45) Date of Patent: May 10, 2022

(54) WEARABLE DEVICE WITH CONSTRICTION ELEMENTS FOR TREATMENT OF ERECTILE DYSFUNCTION

(71) Applicant: Maqsood Jafri, Glen Carbon, IL (US)

(72) Inventor: Maqsood Jafri, Glen Carbon, IL (US)

( * ) Notice: Subject to any disclaimer, the term of this patent is extended or adjusted under 35 U.S.C. 154(b) by 171 days.

(21) Appl. No.: 16/801,484

(22) Filed: Feb. 26, 2020

(65) Prior Publication Data

US 2020/0188220 A1 Jun. 18, 2020

Related U.S. Application Data

(63) Continuation of application No. 15/355,223, filed on Nov. 18, 2016.

(51) Int. Cl.
| | |
|---|---|
| *A61F 5/41* | (2006.01) |
| *A61H 19/00* | (2006.01) |
| *A61H 9/00* | (2006.01) |
| *A61H 23/02* | (2006.01) |

(52) U.S. Cl.
CPC ............... *A61H 19/32* (2013.01); *A61F 5/41* (2013.01); *A61H 9/0057* (2013.01); *A61H 9/0078* (2013.01); *A61H 23/02* (2013.01); *A61F 2005/411* (2013.01); *A61F 2005/414* (2013.01); *A61F 2005/415* (2013.01); *A61F 2005/417* (2013.01); *A61H 2201/5071* (2013.01)

(58) Field of Classification Search
CPC .......... A61F 2005/411; A61F 2005/414; A61F 2005/415; A61F 2005/417; A61F 5/41; A61H 19/32
See application file for complete search history.

(56) References Cited

U.S. PATENT DOCUMENTS

| | | | | |
|---|---|---|---|---|
| 4,407,275 A | * | 10/1983 | Schroeder | A61F 5/41 600/38 |
| 2006/0229494 A1 | | 10/2006 | Wu | |
| 2011/0172489 A1 | | 7/2011 | Muller | |
| 2013/0253264 A1 | * | 9/2013 | Canbulat | A61H 19/32 600/38 |

(Continued)

FOREIGN PATENT DOCUMENTS

WO 2004084779 A1 10/2004

*Primary Examiner* — Christine H Matthews
(74) *Attorney, Agent, or Firm* — Williams Intellectual Property; Benjamin F. Williams

(57) ABSTRACT

A wearable device with constriction elements for treatment of erectile dysfunction includes a sheath member having a proximal annual section and a distal annular section configured to tautly engage around a user's penis. At least one channel is disposed within at least one longitudinal section disposed interconnecting the proximal and distal annular sections. The at least one channel is disposed to accommodate one or more of an elongate rod member, at least one vibratory unit, or introduction of compressed air forcibly introduced therein to rigidify and mechanically support the wearer's penis. At least one inflatable constriction ring is disposed seatable into the proximal and/or distal constriction ring to target penile blood vessels and prevent blood loss therefrom. A vibratory sleeve is also included, devised to assist in inducing an erection by manual application around a user's penis and mechanical action of a plurality of elongate vibratory units disposed therein.

14 Claims, 7 Drawing Sheets

(56) References Cited

U.S. PATENT DOCUMENTS

2014/0171734 A1    6/2014    Kassman
2014/0224263 A1*  8/2014    Wilson ..................... A61F 5/41
                                                                  131/186

* cited by examiner

WEARABLE DEVICE WITH CONSTRICTION ELEMENTS FOR TREATMENT OF ERECTILE DYSFUNCTION

CROSS-REFERENCE TO RELATED APPLICATIONS

This continuing application claims the benefit of application Ser. No. 15/355,223, filed on Nov. 18, 2016.

FEDERALLY SPONSORED RESEARCH OR DEVELOPMENT

Not Applicable

INCORPORATION BY REFERENCE OF MATERIAL SUBMITTED ON A COMPACT DISK

Not Applicable

SPECIFICATION

To Whom it may Concern

Be it known that I, Maqsood Jafri, a citizen of the United States, have invented new and useful improvements in a wearable device with constriction elements for treatment of erectile dysfunction as described in this specification.

BACKGROUND OF THE INVENTION

The present invention relates to a wearable device with constriction elements usable for the treatment of the symptoms of erectile dysfunction. The device essentially provides structural support for a user, when worn on the user's penis, and constricts outflow of blood from the penis by taut engagement of annular sections and, in at least one embodiment, inflatable constriction rings, to prevent leakage of blood via the penile veins whereby an erection may be sustained during sexual intercourse.

According to the Urology Care Foundation, as many as 30 million men suffer from erectile dysfunction in the United States alone. Primary causes for erectile dysfunction are physiological, and involve limitations to blood flow in the penis, or damage to the penile nerves or blood vessels. Psychological reasons, such as stress, anxiety, or other emotional problems, may also play a part for some patients.

The present invention, therefore, addresses the primary causes of erectile dysfunction by providing means to constrict blood outflow from the penis after an erection is maintained. Stimulation provided mechanically by the action of vibratory units as well by manual manipulation with the aid of a vibratory sleeve, may also assist in attaining an erection.

FIELD OF THE INVENTION

The present invention relates to a wearable device with constriction elements for treatment of erectile dysfunction. The device essentially provides structural support for a user, when worn on the user's penis, and provides constriction to prevent leakage of blood via the penile veins. The present device assists in attaining and then maintaining an erection. Some embodiments include means for stimulating the user's penis, such as vibratory units caused to oscillate in close contact with the user's penis and provide mechanical stimulation to penile nerves. At least one embodiment includes a vibratory sleeve usable to induce an erection previous to applying a sheath member and/or at least one constriction ring.

A handheld control system is included to enable controlled inflation of at least one inflatable constriction ring, proximal and distal annular sections (when inflatable), as well as to manually control operation, intensity, and frequency of vibratory stimulation when at least one vibratory unit is operatively coupled with the device.

The present device, therefore, assists in the treatment of symptoms associated with erectile dysfunction, enabling a user to attain an erection while assisting the user to maintain said erection before and during sexual intercourse.

SUMMARY OF THE INVENTION

The wearable device with constriction elements for the treatment of erectile dysfunction has been devised to assist a user achieve and maintain an erection during sexual intercourse. A sheath member is configured to secure around a user's penis positioning a proximal annular section tautly seated circumferentially around the user's penis approximal a base of the user's penis and a distal annular section tautly seated circumferentially around the user's penis approximal a glans of the said user's penis. The proximal and distal annular sections may be elastomeric or inflatable and are devised to tighten around the user's penis once an erection is achieved. The proximal annular section is disposed to constrict outflow of blood from the corpora cavernosa of the user's penis and the distal annular section is disposed to constrict outflow of blood from the glans of the user's penis.

At least one polymeric longitudinal section is disposed interconnecting the proximal and distal annular sections. The at least one longitudinal section has a channel therein wherein is insertable at least one of the following: compressed air, an elongate rod, and/or at least one vibratory unit. When air is compressed into the channel, by action of a manual control system as will be described subsequently, the channel is pressurized and the sheath is caused to rigidify, at least longitudinally along the channel. Insertion of the elongate rod into the channel likewise enables structural support longitudinally along the sheath member. Inclusion of at least one vibratory unit—which may include an elongate vibratory unit, and thereby serve to structurally strengthen the channel as well—enables stimulation of the user's penis whenever the at least one vibratory unit is activated by means of the manual control system, as will be described subsequently.

The sheath member is thus fittable upon the user's penis to assist in developing and maintaining an erection by stimulation of mechanical forces, constriction to impede drainage of blood from the corpus spongiosum and corpora cavernosa, and via structural support.

In at least one embodiment contemplated herein, at least one inflatable constriction ring is contemplated securable in conjunction with the proximal and/or distal annular sections circumferentially girding a user's penis. This at least one constriction ring is configured for inflation to tautly engage around the user's penis as tightly as the user desires between a minimum inflation and a maximum inflation. The level of inflation is controllable by action of the manual control system, as will be described subsequently, and enables prevention of outflow of blood from the user's penis when the constriction ring is inflated. The user may inflate the constriction ring to a desired tightness once an erection has been achieved and thereby prevent outflow of blood thereafter. Further, controlling inflation of the at least one constriction ring enables adjustment of said constriction ring to engage tautly around penises of differing girths or to vary constriction at different moments during foreplay and/or sexual intercourse.

To provide increased and direct pressure to particular blood vessels and tissues of the user's penis, the at least one inflatable constriction ring may include at least one protuberance, disposed to project toward the center of said ring, which is configured to apply increased pressure upon tissue immediately in contact therewith, thereby to impede blood flow within particular targeted tissue of the user's penis. The at least one protuberance is devised to impede blood flow through the superficial dorsal vein, the deep dorsal vein, and the bulbourethral vein, for example, among other dorsal, dorsolateral, basal, basolateral and other penile veins and blood vessels, as case may be, and thereby maintain blood pressure within the corpus spongiosum and the corpora cavernosa.

In at least one embodiment, the at least one protuberance is an elongate expanse devised to cover dorsal and dorsolateral areas of the user's penis and apply additional pressure thereto. In another embodiment, the at least one protuberance includes a plurality of protuberances devised as spheroidal projections disposed in a configuration appropriate to engage against portions of the user's penis and directly compress underlying tissue to impede blood flow through the dorsal and dorsolateral penile veins, as well as basal, basolateral, and other penile veins in some embodiments. The particular shape of the at least one protuberance may be rounded, conic, elongate, or other raised shaped suitable for applying pressure to targeted areas of the user's penis.

In order to maintain patency of the urethra once inflated, the at least one inflatable constriction ring may further include at least one groove disposed upon an inner surface of the at least one inflatable constriction ring. The groove is disposed to accommodate the user's urethra thereunder, wherein the at least one inflatable constriction ring does not impede patency of the user's urethra or the passage of ejaculate therethrough when the at least one constriction ring is inflated.

In another embodiment of the at least one constriction ring contemplated herein, the ring may comprise a hoop, having an open section devised to seat over the user's urethra whereby the urethra remains unimpeded when the at least one constriction ring is inflated to compress the corpora cavernosa. In at least one embodiment, a connecting member may interconnect the ends of the hoop-shaped at least one constriction ring, said connecting member attached to the outermost surface of end sections of the hoop-shaped at least one constriction ring, thereby strengthening the constriction ring and preventing of the ends of the constriction ring from widening apart when the constriction ring is inflated.

A handheld control system is configured for manual operation of the wearable device with constriction elements. The handheld control system is disposed in operational communication with the at least one vibratory unit and/or the channel and/or with the proximal and distal annular sections of the sheath member in example embodiments when said proximal and distal annular sections are inflatable. The handheld control system may include a keypad, or the like, whereby selection of controls upon the handheld control system engage and disengage the vibratory unit, for example. The handheld control system may operate wirelessly. The handheld control system may be wired to the sheath member and connected to the sheath member at the base thereof, approximal the proximal annular section, whereby power may be conveyed from batteries, or other power source, housed in or relayed through the handheld control system.

In another embodiment contemplated herein, the manual control system may include at least one manual pump member disposed connectable to the sheath member via tubing to compress air into the channel and the proximal and distal annular sections (where inflatable) to rigidify and lengthen the sheath member by action of compressed air forced into the channel of the sheath member. The at least one pump member may likewise be connectable to the at least one constriction ring to enable manual inflation thereof. In an alternative embodiment contemplated herein, the at least one pump member includes a plurality of pump members directly connectable to the sheath member and the at least one constriction ring. A release valve may be disposed upon the sheath member, the at least one constriction ring, or upon connectable tubing that connects directly to the sheath member and/or the constriction ring, whereby sudden release of the pressure within the channel, the proximal and distal annular sections (where inflatable), and/or the at least one constriction ring is enabled by manually contacting the release valve. A pressure gauge may be included to signal the pressure attained within the channel, the proximal and distal annular sections (where inflatable) and, where operative, the pressure within the at least one constriction ring.

Alternatively, the sheath member may include a plurality of micro-pumps that enable automated compression of air into the channel, the proximal and distal annular sections (where inflatable), and/or at least one constriction ring when fitted to the sheath member. The at least one constriction ring may therefore be devised to seat into the proximal and/or distal annular section in such a manner that a one-way valve is positioned to contact an inlet disposed interiorly upon the sheath member, wherein operation of the plurality of micro-pump pressurizes air into the at least one constriction ring. The one-way valve, disposed upon the at least one constriction ring, may be releasable manually to alleviate the pressure, as desired.

The sheath member may further include a beaded elasticated band, attachable proximal the proximal annular section of the sheath member, and there disposed for taut and releasable engagement around the user's testicles. In this configuration, ends of the beaded elasticated band are connectable to the sheath member proximal the proximal annular section whereby the beaded elasticated band depends underlying the proximal annular section of the sheath member. When the device is fitted to the user's penis, the beaded elasticated band is fittable around the testicles of the user and may be tightened to engage the testicles tautly by sliding a snap-band, that tensions the beaded elasticated band together, along the elasticated band and thereby shorten the effective circumference of said elasticated band as desired.

In at least one embodiment, a vibrator sleeve is included to apply stimulation to the penis and aid in inducing an erection thereby. The vibrator sleeve has been devised to position a plurality of elongate vibratory units in close contact with the user's penis, to apply vibratory stimulation along the length of the user's penis, and thereby induce an erection. The vibrator sleeve may be controllable by action initiated at the handheld control unit whereby the frequency and intensity of vibrations may be varied, as desired, to assist in inducing an erection. The vibrator sleeve is contemplated to be usable in tandem with the sheath member whereby a user may induce an erection and then maintain the erection by application of the sheath member and/or constriction ring(s) to enable intercourse after an erection has been secured.

Thus has been broadly outlined the more important features of the present wearable device with constriction elements for treatment of erectile dysfunction so that the detailed description thereof that follows may be better understood and in order that the present contribution to the art may be better appreciated.

Objects of the present wearable device with constriction elements for treatment of erectile dysfunction, along with various novel features that characterize the invention are particularly pointed out in the claims forming a part of this disclosure. For better understanding of the wearable device with constriction elements for treatment of erectile dysfunction, its operating advantages and specific objects attained by its uses, refer to the accompanying drawings and description.

BRIEF DESCRIPTION OF THE DRAWINGS

Figures

DETAILED DESCRIPTION OF THE DRAWINGS

With reference now to the drawings, and in particular FIGS. 1 through 14A, 14B, and 14C, thereof, example of the instant wearable device with constriction elements for treatment of erectile dysfunction employing the principles and concepts of the present wearable device with constriction elements for treatment of erectile dysfunction and generally designated by the reference number 10 will be described.

In all embodiments, the sheath member 20 is devised of a yielding, elastomeric or polymeric material, devised to be thin and hypoallergenic, such as, for example, silicone, latex, or other thin, elastomeric or rubberlike substance.

Figure 1:
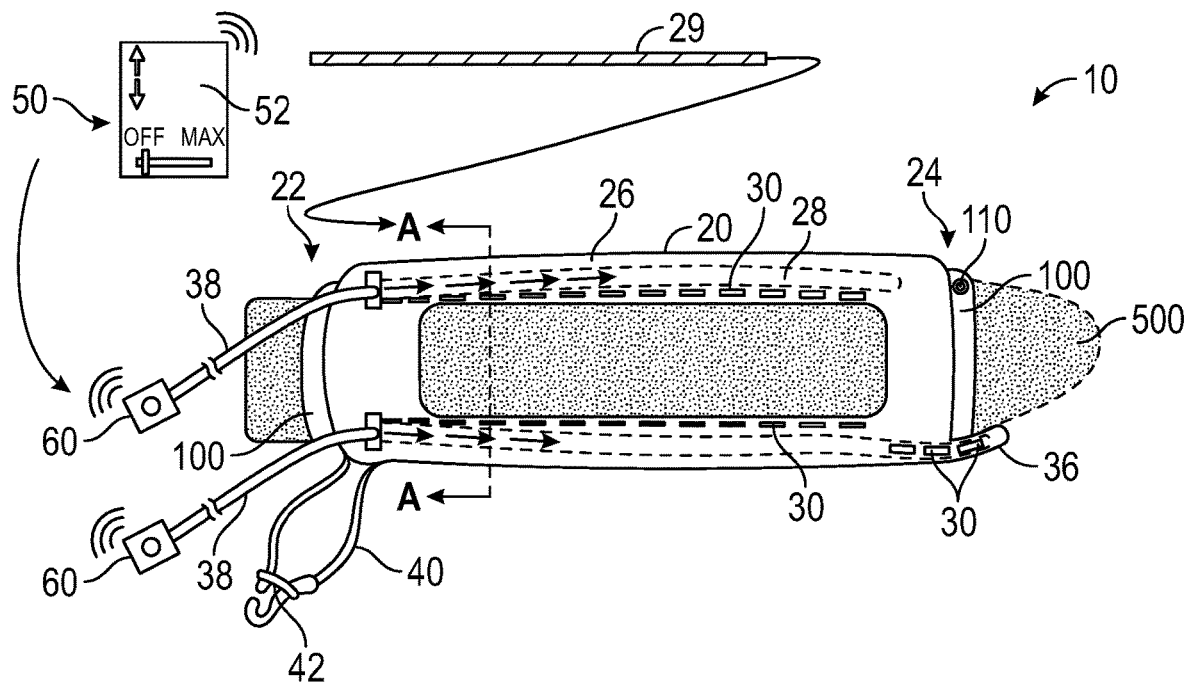
FIG. 1 is a side elevation in-use view of an example embodiment of a sheath member.
Figure 3:
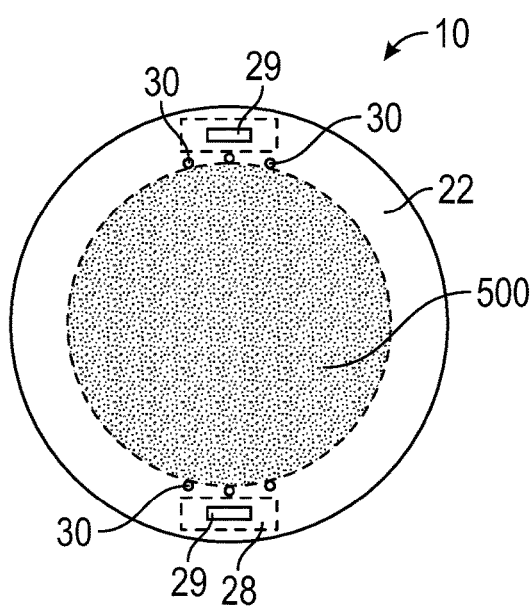
FIG. 3 is an example embodiment of a transverse cross-section view taken along line A-A through the proximal annular section of the apparatus depicted in FIG. 1 having an elongate rod inserted interior to the channel.

FIG. 1 depicts a side elevation view of an example embodiment of the wearable device with constriction elements for treatment of erectile dysfunction 10 worn by a user. The sheath member 20 includes proximal annular section 22 and distal annular section 24. At least one longitudinal section 26 includes upper and lower longitudinal sections, each having a channel 28 wrought interior thereto. In one embodiment contemplated herein, each said channel 28 is disposed to receive an elongate rod member 29 installable therein. In another embodiment contemplated herein, each said channel 28 is disposed to receive at least one vibratory unit or 30 capable of stimulating the wearer of the device 10. As shown in FIG. 3, at least one embodiment of the present invention 10 incudes vibratory units 30 operationally coupled to at least one elongate rod 29 for insertion interior to each said at least one elongate channel 28.

In at least one embodiment contemplated herein, the at least one channel 28 may be inflatable by maintaining compressed air forced therein. In such an embodiment, at least one micro-pump 60 may be used to compress air into the at least one channel 28 and thereby provide structural support via inflation to a person wearing the apparatus. (Where more than one channel 28 is extant, a single pump 60 may be configured to inflate more than one channel 28.) FIG. 1 depicts interconnecting members 38 which may comprise detachable tubing for pressurizing compressed air into each at least one channel 28 (see for example FIG. 5 for alternative inflation by action of at least one manual pump 54) and, alternatively, as shown in FIG. 1, connections for a handheld control 50 for controlling the operation of vibratory units 30 and micro-pumps 60, in both frequency and intensity as well as switching the vibratory units 30 on and off. Frenulum extension 36 provides support and, in at least one embodiment, stimulation to the frenulum of the wearer. Handheld control system 50 may include a keypad 52 for manual selection between various controls to inflate and vibrate the sheath member 20 and at least one constriction ring 100. Keypad 52 may be wirelessly communicative with the sheath member 20 or maybe connected via interconnecting members 38, as case may be.

In the example embodiment depicted in FIG. 1, at least one constriction ring 100 is disposed seated into the proximal annular section 22, and at least one constriction ring 100 is disposed seated into the distal annular section 24. In the example embodiment depicted, each said at least one constriction ring 100 is contemplated to be inflatable by interconnection with the handheld control system 50 or manual pump 54 with valve. Beaded elasticated band 40 is included in this example embodiment for taut engagement around the scrotum of a wearer, which tautness is variable by action of snap-band 42 slidingly engaging around the beaded elasticated band 40 to effectively shorten its actionable circumference.

Figure 2:
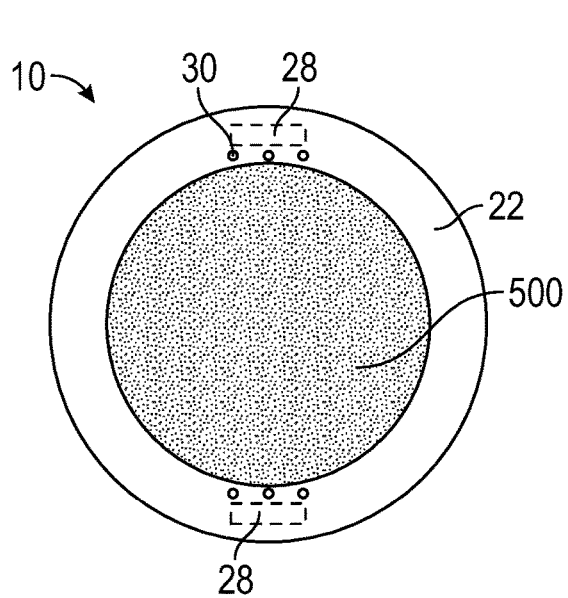
FIG. 2 is an example embodiment of a transverse cross-section view taken along line A-A through a proximal annular section of the apparatus depicted in FIG. 1 depicting a channel.

FIGS. 2 and 3 depict transverse cross-section views of the proximal annular section 22 taken along line A-A of FIG. 1, and show the at least one channel 28 in FIG. 1 for insertion of the elongate rod member 29 or, in other embodiments inflation, and, in FIG. 3, the vibratory units 30 operationally coupled with the elongate rod member 29.

Figure 4:
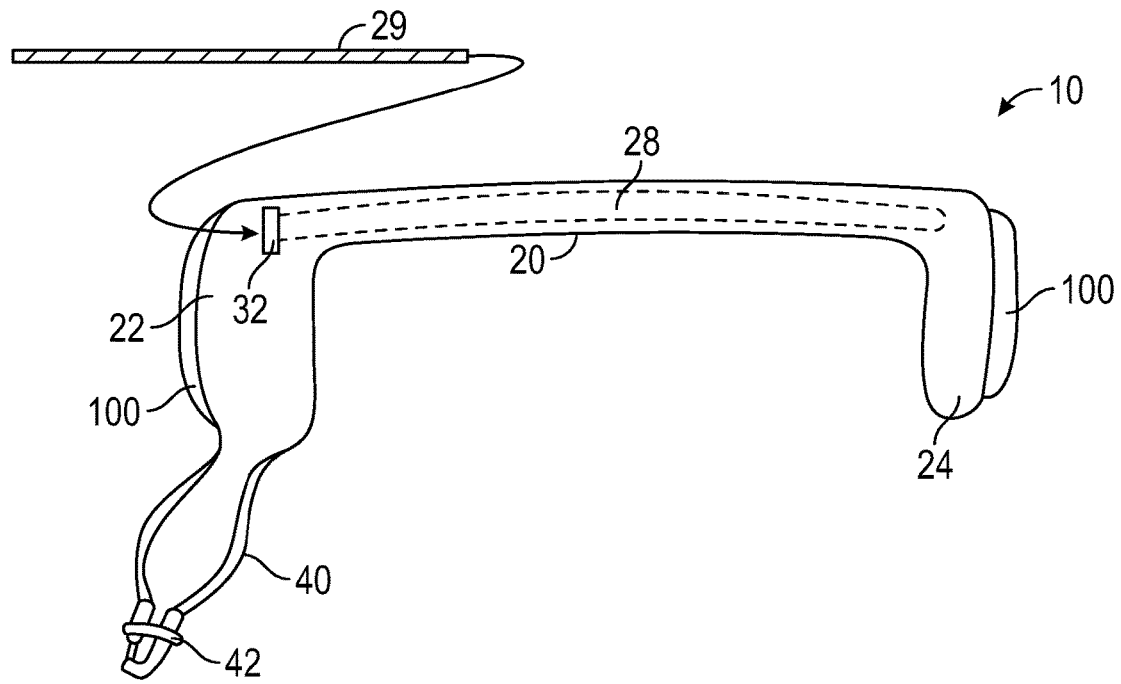
FIG. 4 is a side elevation view of an example embodiment having only one longitudinal section disposed between the proximal annular section and the distal annular section.

FIG. 4 depicts a side elevation view of an example embodiment having a single longitudinal section 26 configured for disposition dorsally upon the penis 500 of a wearer. Proximal and distal annular sections 22, 24 are alike as already described in regard to FIG. 1 above, and at least one constriction ring 100 is seated into each of the said proximal and distal annular sections 22, 24, there inflatable to tautly engage around the penis 500 of a wearer and prevent blood loss from diminishing an erection attained. In this embodiment, the at least one channel 28 is a single channel disposed in the at least one longitudinal section 26, which includes slit 32 for insertion of elongate rod member 29 or, in alternative embodiments, interconnection with a manual pump 54 or handheld control system 50 to effectuate inflation of the said channel 28.

Figure 5:
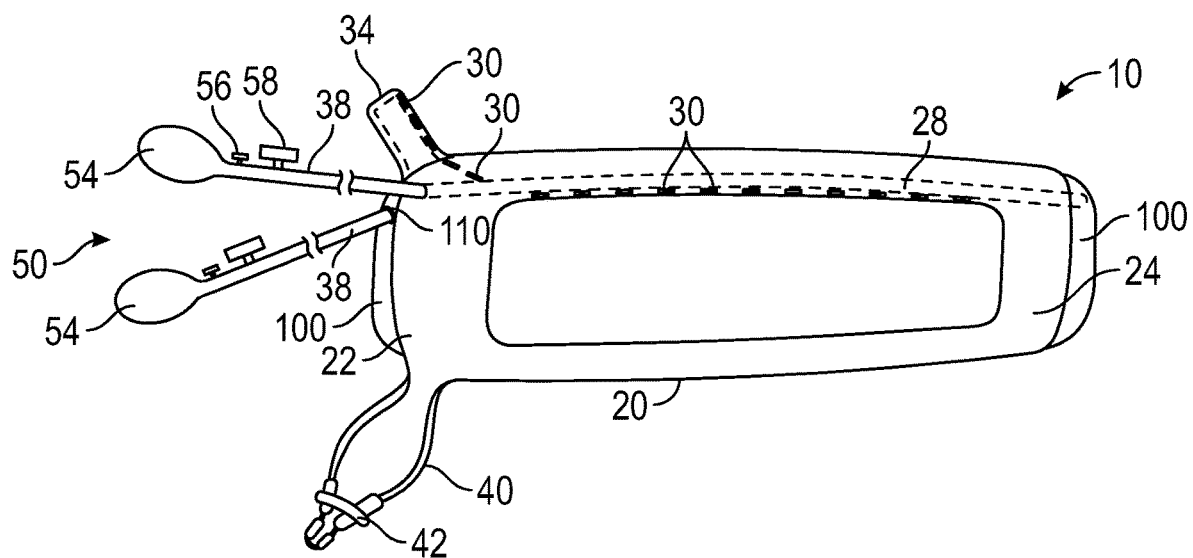
FIG. 5 is a side elevation view of an example embodiment having at least one manual pump connected to the sheath member.

FIG. 5 depicts a side elevation view of an example embodiment wherein the at least one channel 28 is inflatable via interconnection with at least one manual pump 54. Each at least one manual pump 54 is manually compressible to force air into the at least one channel 28 with which said at least one manual pump 54 is interconnected. The at least one manual pump 54 is readily disconnected once a desired pressure has been attained interior to the at least one channel 28.

Another at least one manual pump 54 is illustrated connected to the valve 110 of the constriction ring 100 seated at the proximal annular section 22. Once a desired pressure has been attained and the constriction ring 100 inflated, the said at least one manual pump 54 may be detached. In the example embodiment shown, each at least one manual pump 54 includes a pressure gauge 58, providing a pressure readout to the user, and a pressure release valve 56 by which the associated constriction ring 100 or at least one channel 28 may be depressurized.

Pocket 34 may be included for storing interconnection members 38 to interconnect the at least one manual pump 54, when not in use. Pocket 34 may also act to stimulate a partner during intercourse, in position to contact the clitoris during ventro-ventral sexual intercourse between a man and a woman.

Figure 6:
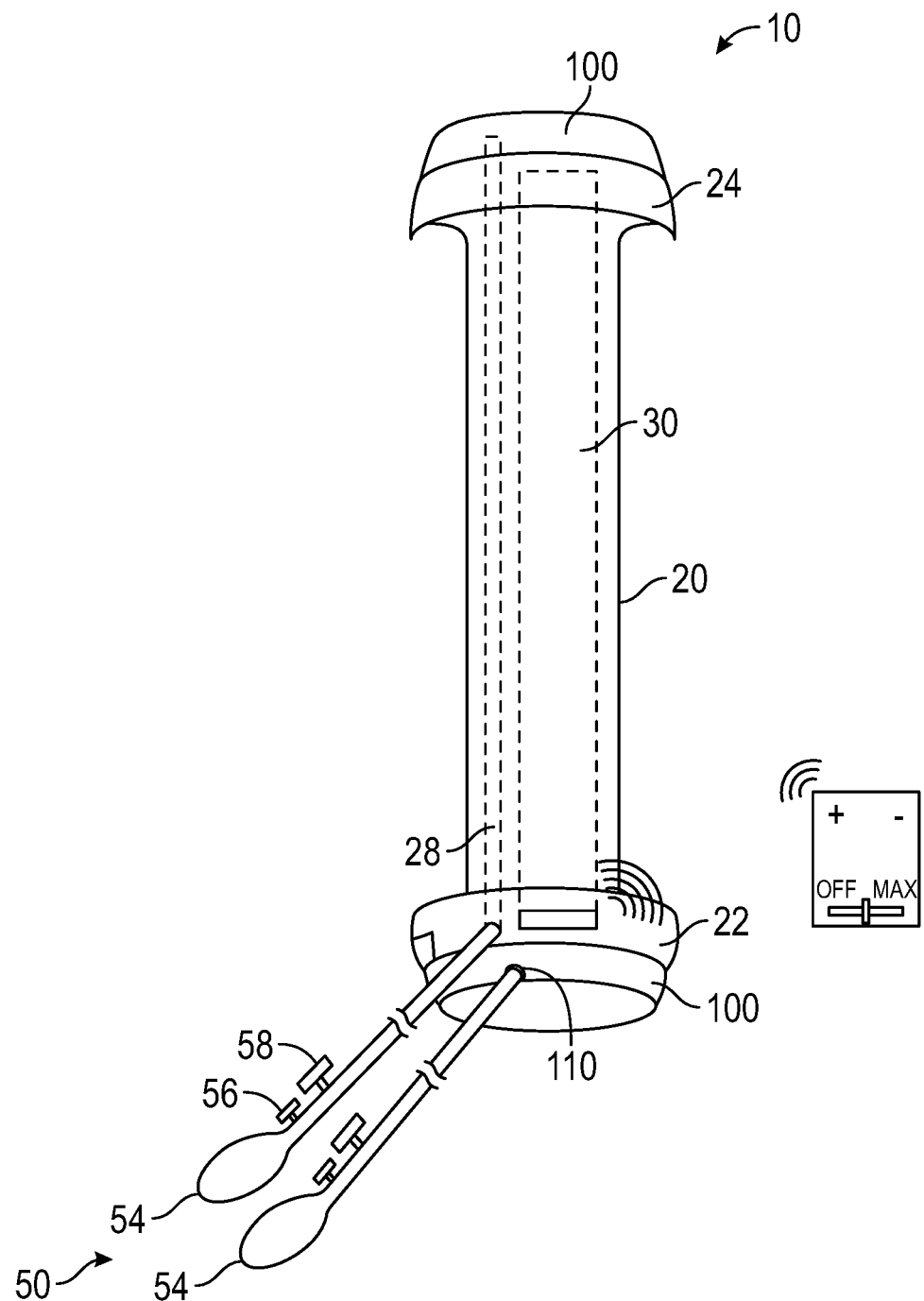
FIG. 6 is a top elevation view of an example embodiment with a vibratory unit disposed therein.

FIG. 6 depicts a top elevation view of an example embodiment. In this example embodiment, the at least one longitudinal section 26 includes a parallelepiped vibratory unit 30 disposed therein to provide stimulation dorsally when the device is worn. Channel 28 is inflatable to increase support and rigidity of the sheath member 20. In the example embodiment shown, channel 28 may be disposed in open communication with the at least one constriction ring 100 disposed at the distal annular section 24, whereby pressurization and inflation of the channel 28 also inflates the at least one constriction ring 100 disposed at the distal annular section 24. The at least one constriction ring 100 disposed at the proximal annular section 22 may be connected directly to manual pump 54 (as shown) or it may also be inflatable via open communication with channel 28.

Figure 7:
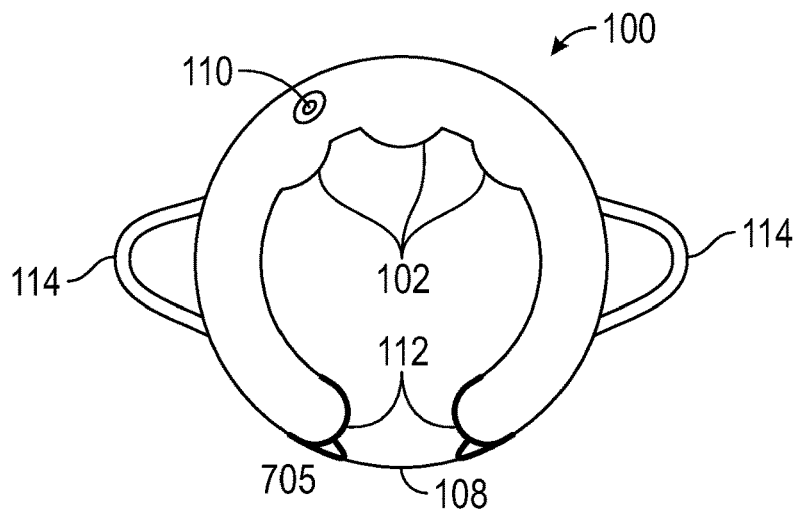
FIG. 7 is a front elevation view of an example embodiment of an inflatable hoop-shaped constriction ring with connecting member disposed connecting ends thereof.

FIG. 7 is a top elevation view of an example embodiment of at least one constriction ring 100. In this example embodiment, the at least one constriction ring 100 is disposed in the form of a hoop. A connecting member 108 is disposed interconnecting end sections 112 of the hoop-shaped constriction ring 100. This connecting member 108 may be attachable and may assist in preventing splaying of end sections 112 of the hoop-shaped constriction ring 100 from parting during inflation and during use. The connecting member 108 may also enable an amount of adjustability in maintaining proximity of end sections 112 together.

At least one protuberance 102 is shown disposed upon the interior curvature of the ring 100. Each said at least one protuberance 102 is situated to target blood vessels, such as the superficial dorsal vein, the cavernosal vein, the deep dorsal vein, associated para-arterial veins, and other veins, to prevent leakage of blood flow from the corpora cavernosa and other penile tissue, and thereby to help sustain an erection. In this particular depiction as illustrated, the at least one protuberance 102 includes three protuberances disposed to impress upon the wearer's penis dorsally and dorsolaterally. FIG. 7 also illustrates a pair of auricular members 114 usable to assist in positioning the constriction ring 100 around the penis, whether situated at the proximal annular section 22 or distal annular section 24, or whether used without the sheath member 20, as case may be.

Figure 8:
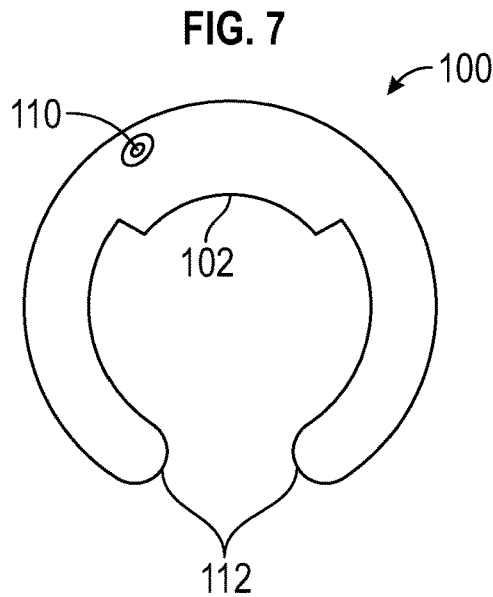
FIG. 8 is a front elevation view of an example embodiment of an inflatable hoop-shaped constriction ring elongate protuberance disposed inward facing thereupon.
Figure 9:
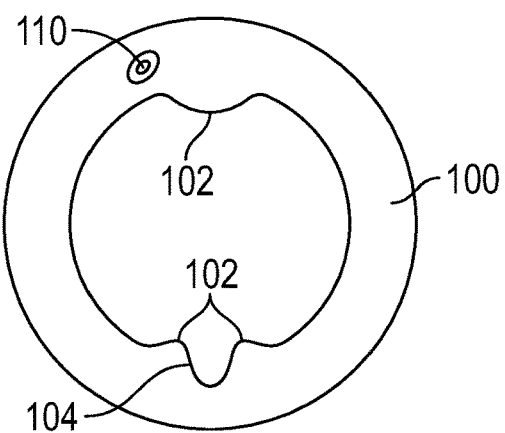
FIG. 9 is a front elevation view of an example embodiment of an inflatable constriction ring having a plurality of protuberances disposed inward facing thereupon, and a groove disposed to accommodate a user's urethra when the constriction ring is worn.

FIG. 8 is a top elevation view of another example embodiment of a hoop-shaped constriction ring 100. In this embodiment, the at least one protuberance 102 is disposed as a continuous cushion disposed to gird and impress dorsolaterally upon the wearer to constrain leakage from the superficial dorsal vein, the deep dorsal vein, the cavernosal vein, and associated para-arterial veins and other veins as case may be. FIG. 9 is a top elevation view of an example embodiment of at least one constriction ring 100 having at least one protuberance 102 disposed to impress dorsally upon the wearer and another protuberance 102 disposed to impress basally upon the wearer to constrain leakage of blood from the burbourethral vein, and other veins disposed basally within the wearer's penis. Groove 104 is disposed to accommodate the user's urethra, to maintain patency of the urethra and enable unimpeded passage of ejaculate during orgasm.

Figure 10:
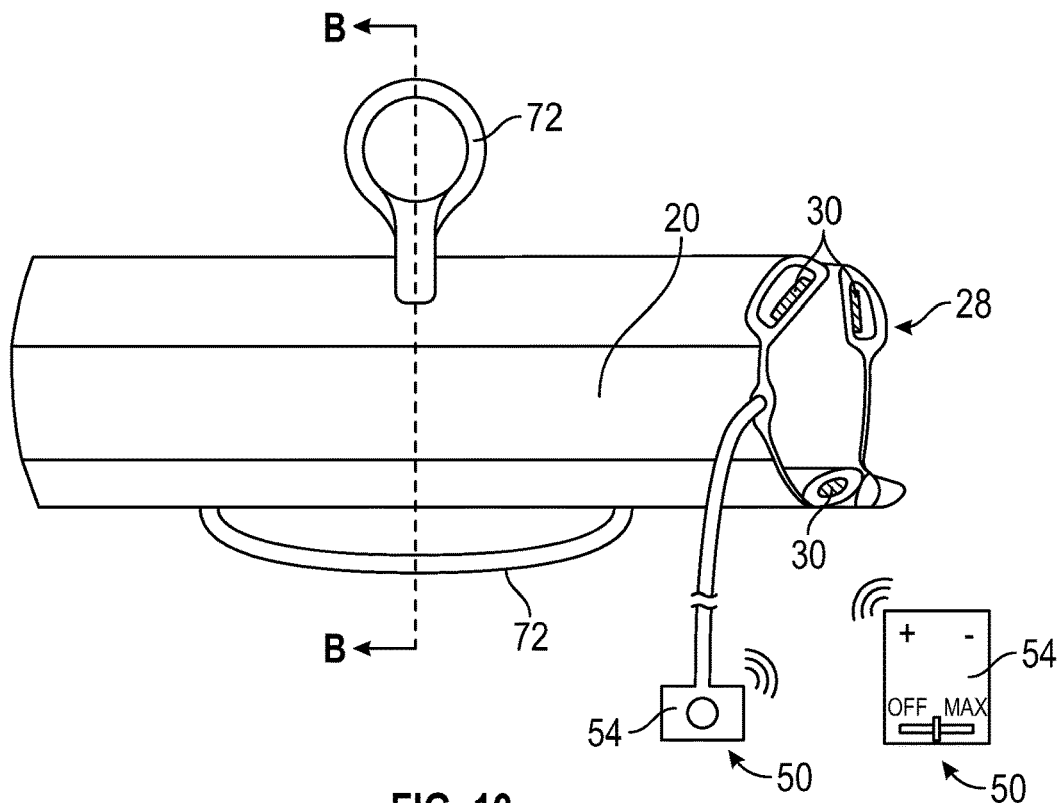
FIG. 10 is a side elevation view of a vibrator sleeve usable to apply stimulation manually and mechanically, by aid of elongate vibratory units, to induce an erection in a user.
Figure 11:
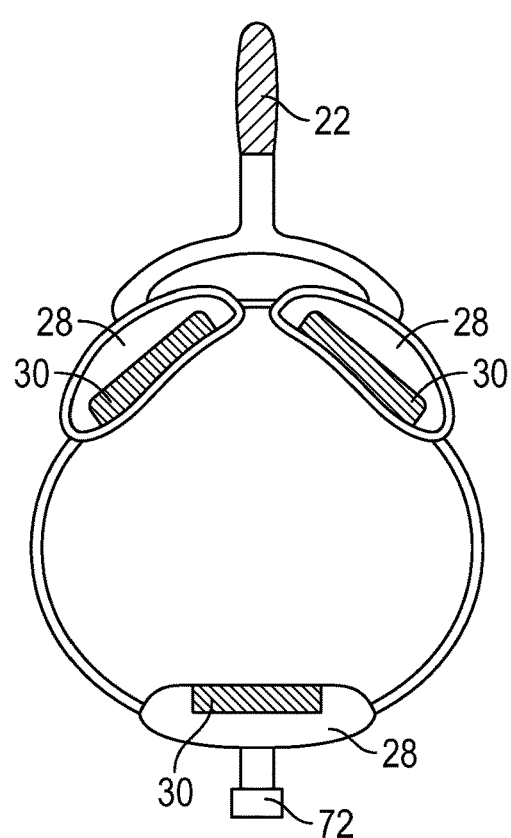
FIG. 11 is a transverse cross-section of the vibrator sleeve depicted in FIG. 10 taken along the line B-B.

FIG. 10 is a side elevation view of an example embodiment of a sheath member 20 disposed as a vibrator sleeve 70 configured to stimulate a user and induce an erection. The sheath member 20 includes a plurality of vibratory units 30 disposed longitudinally in separate channels 28 running the length of the vibrator sleeve 70. Vibratory units 30 are disposed dorsolaterally, in position to stimulate the dorsal nerves of the user's penis. At least one vibratory unit 30 is disposed basally along the length of the sheath member 20 to stimulate the perineal nerves of the user's penis. Handle members 72 are included to enable manual purchase and manipulation of the vibrator sleeve 70 to manually assist in applying the device as well as increase stimulation to induce and sustain an erection. The vibrator sleeve 70 is contemplated to be manufactured from a thin, smooth, elastomeric polymer, such as, for example, silicone or another rubberlike polymer suited to the purpose. Handheld control system 50 may include at least one keypad 54 disposed in wired or wireless communication with the vibratory units 30. FIG. 11 is a transverse cross-section view of the vibrator sleeve depicted in FIG. 10, taken along the line B-B of FIG. 10.

Figure 12:
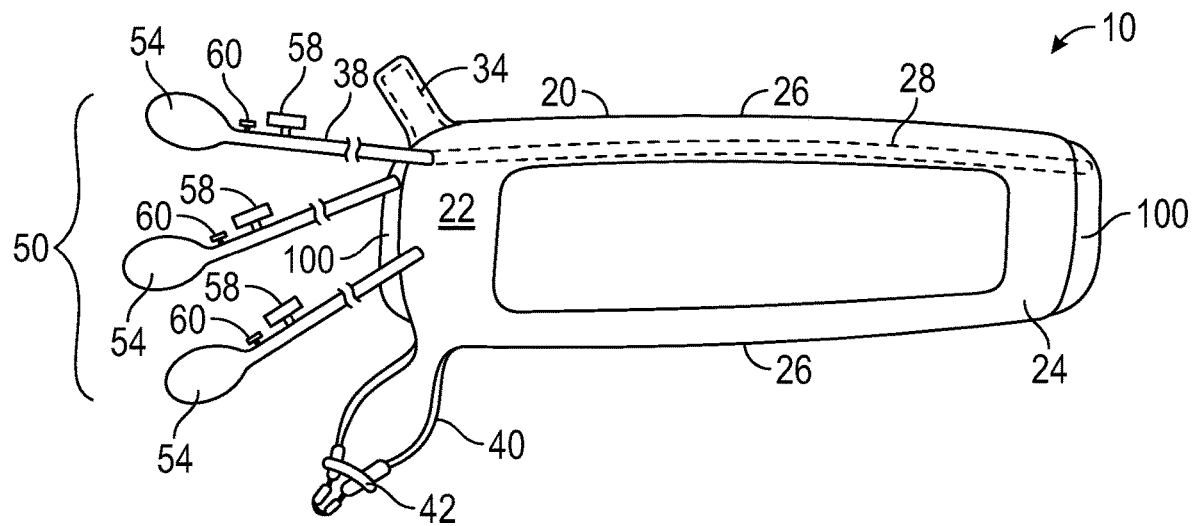
FIG. 12 is a side elevation view of an example embodiment of a sheath member having a plurality of manual pumps installed to effectuate inflation and a pocket disposed for storage of interconnecting tubing and to provide stimulation to a female partner during sexual intercourse.
Figure 13:
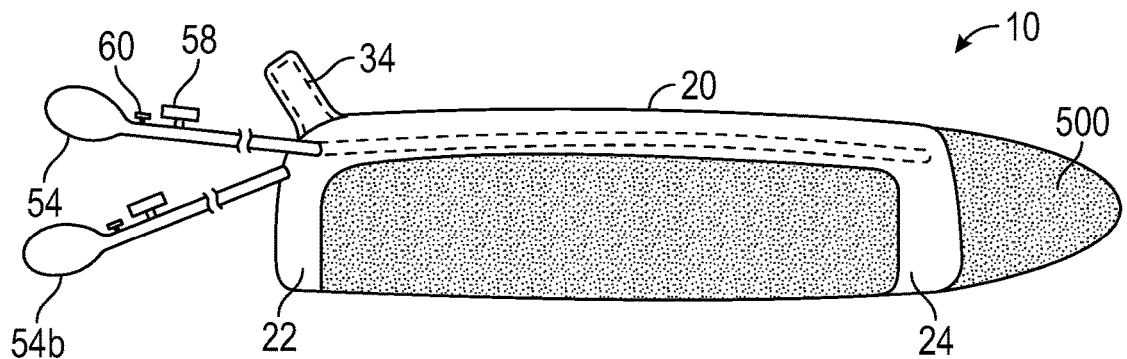
FIG. 13 is a side elevation view of an example embodiment of a sheath member having a plurality of manual pumps installed to effectuate inflation.

FIGS. 12 and 13 illustrate alternative embodiments of the present invention 10 with features already discussed hereinabove. FIG. 13 illustrates an example embodiment of a sheath member 20 usable independent of the at least one constriction ring 100, wherein the proximal and distal annular sections serve as constricting elements elastomerically. Note that manual pump 54b is applied to directly inflate at least the proximal annular section 22 in this embodiment, thereby to tighten the annular section 22 around the base of the user's penis.

Figure 14A:
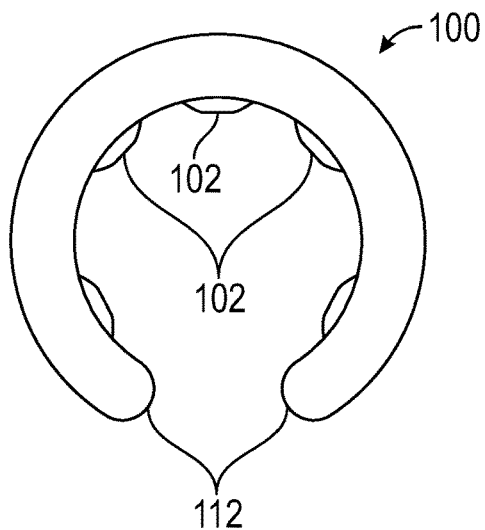
FIGS. 14A, 14B, and 14C depict front elevation views of a hoop-shaped constriction ring having particular protuberances disposed thereupon.
Figure 14B:
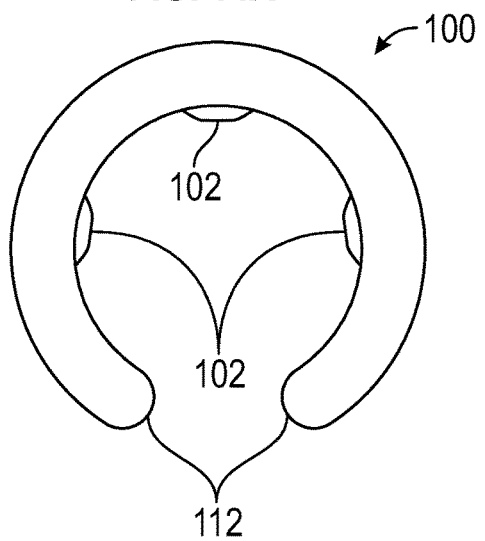
Figure 14C:
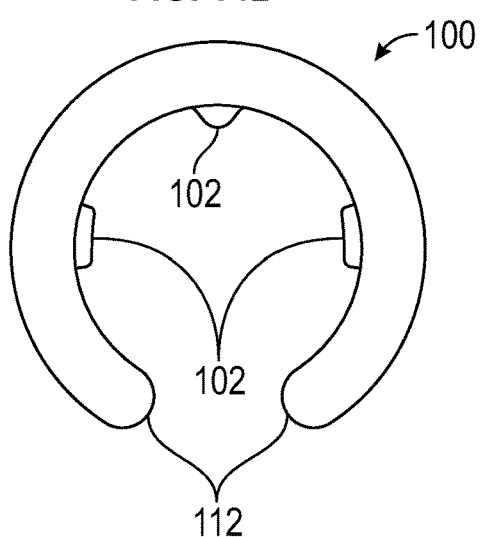

FIGS. 14A, 14B, and 14C illustrate alternative embodiments of the at least one constriction ring 100, depicting a variety of protuberances 102 disposed to impress against targeted tissue and blood vessels in the user's penis. Protuberances 102 are devised in a variety of shapes, from rounded to conical, devised to apply degrees of pressure to the underlying targeted tissue. It is contemplated as within scope of this disclosure, and within the understanding of a person of ordinary skill in the art, that additional arrangements of protuberances 102 and forms of the at least one constriction ring 100 are readily contemplated, the examples provided are intended to exemplify embodiments only, and are not intended to be provided as limiting species of the subject invention 10.

What is claimed is:

1. A wearable system for the treatment of erectile dysfunction comprising:
    a sheath member configured to secure around a user's penis, said sheath member comprising:
        a proximal annular section configured to tautly seat circumferentially around the user's penis to abut a base of the user's penis and continually constrict outflow of blood from the corpora cavernosa of the user's penis;
        a distal annular section configured to seat circumferentially around the user's penis to abut a glans of the user's penis and continually constrict outflow of blood from the glans of the user's penis; and
        at least one longitudinal section disposed interconnecting the proximal and distal annular sections, said at least one longitudinal section comprising a channel therein wherein is insertable:
            compressed air, an elongate rod, and/or at least one vibratory unit;
    wherein the sheath member is fittable upon the user's penis to assist in developing and maintaining an erection by stimulation, constriction, and support.

2. The wearable system for the treatment of erectile dysfunction of claim 1 further comprising at least one inflatable constriction ring securable in conjunction with either or both of the proximal and/or distal annular sections configured to circumferentially gird a user's penis, said at least one constriction ring configured for variable inflation between a minimum inflation and a maximum inflation to prevent outflow of blood from the user's penis when the at least one constriction ring is inflated.

3. The wearable system for the treatment of erectile dysfunction of claim 2 wherein the at least one inflatable constriction ring comprises at least one protuberance disposed to project toward the center of the at least one constriction ring, said at least one protuberance configured to impress upon a targeted area upon the user's penis to impede blood flow within targeted tissue of the user's penis.

4. The wearable system for the treatment of erectile dysfunction of claim 3 wherein the at least one inflatable constriction ring further comprises at least one groove disposed upon an inner surface of the at least one inflatable constriction ring, said at least one groove disposed to accommodate the user's urethra wherein the at least one inflatable constriction ring does not impede patency of the user's urethra or passage of ejaculate therethrough when the at least one constriction ring is inflated.

5. The wearable system for the treatment of erectile dysfunction of claim 3 wherein the targeted tissue includes dorsal and dorsolateral penile veins.

6. The wearable system for the treatment of erectile dysfunction of claim 3 wherein the targeted tissue includes basal and basolateral penile veins.

7. The wearable system for the treatment of erectile dysfunction of claim 3 wherein the at least one inflatable ring is not completely circular, said at least one inflatable ring disposed in the shape of a hoop with an open section disposed between a pair of end sections wherein fit of the at least one inflatable constriction ring around the user's penis accommodates the user's urethra between the pair of end sections when the at least one constriction ring is inflated to maintain urethral patency and to enable passage of ejaculate therethrough.

8. The wearable system for the treatment of erectile dysfunction of claim 1 wherein the sheath member further comprises a handheld control system disposed in operational communication with at least one of the following:
    the at least one vibratory unit; and
    the channel;
    wherein the at least one vibratory unit is controllable manually and/or the channel is fillable with compressed air by manual selection.

9. The wearable system for the treatment of erectile dysfunction of claim 2 wherein the sheath member further comprises a handheld control system disposed in operational communication with at least one of the following:
    the at least one vibratory unit;
    the at least one inflatable constriction ring; and
    the channel;
    wherein the at least one vibratory unit is controllable manually and the channel and/or the at least one inflatable constriction ring is fillable with compressed air by manual selection.

10. The wearable system for the treatment of erectile dysfunction of claim 9 wherein the handheld control system includes at least one pump, connectable to the sheath member whereby inflation of the channel and/or the at least one constriction ring is automated when the at least one pump is activated.

11. The wearable system for the treatment of erectile dysfunction of claim 1 wherein the sheath member further comprises a beaded elasticated band disposed proximal the proximal annular section, said beaded elasticated band disposed for taut and releasable engagement around the user's testicles.

12. The wearable system for the treatment of erectile dysfunction of claim 10 wherein the handheld control system communicates with the sheath member wirelessly.

13. The wearable system for the treatment of erectile dysfunction of claim 10 wherein the at least one pump comprises at least one hand pump directly connectable to the sheath member to enable manual compression of air into the channel and/or the at least one constriction ring.

14. The wearable system for the treatment of erectile dysfunction of claim 1 further comprising a separate vibratory sleeve configured to induce and sustain an erection, said vibratory sleeve having a plurality of vibratory units disposed longitudinally therein, said vibratory sleeve devised of a yielding elastomeric polymer configured for sliding engagement around the user's penis to induce and sustain the erection via contact, manipulation, and stimulation.

\* \* \* \* \*